(12) United States Patent
Parthasaradhi Reddy et al.

(10) Patent No.: US 7,361,770 B2
(45) Date of Patent: Apr. 22, 2008

(54) PROCESS FOR PREPARATION OF VALSARTAN

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 458 days.

(21) Appl. No.: 10/539,811

(22) PCT Filed: Jun. 16, 2003

(86) PCT No.: PCT/IN03/00218

§ 371 (c)(1),
(2), (4) Date: Jun. 20, 2005

(87) PCT Pub. No.: WO2004/111018

PCT Pub. Date: Dec. 23, 2004

(65) Prior Publication Data

US 2006/0100443 A1    May 11, 2006

(51) Int. Cl.
*C07D 257/04*    (2006.01)
(52) U.S. Cl. .................. 548/253; 548/250; 548/252
(58) Field of Classification Search ............... 548/250, 548/252, 253
See application file for complete search history.

(56) References Cited

U.S. PATENT DOCUMENTS 5,399,578 A    3/1995   Buhlmayer et al.

5,965,592 A    10/1999  Buhlmayer et al.

FOREIGN PATENT DOCUMENTS

WO    WO 2004/111018 A1    12/2004

OTHER PUBLICATIONS

PCT International Search Report Dated Mar. 10, 2004.
Chemical Abstract No. 137:109453 (Zhongguo Yiyano Gongye Zazhi, 2001, 32(9), 385-387.
Chemical Abstract No. 138:89813 (CN 1317485).
Bio organic & Medicinal Chemistry Letters, vol. 4, No. 1, 29-34 (1994).

*Primary Examiner*—Golam M. M. Shameem
(74) *Attorney, Agent, or Firm*—Caesar, Rivise, Bernstein, Cohen & Pokotilow, Ltd.

(57) ABSTRACT

Valsartan of formula (I) is prepared by hydrolysis of valsartan benzyl ester with an alkali metal hydroxide, washing with an organic solvent, acidifying with hydrochloric acid and isolating valsartan from the reaction mixture

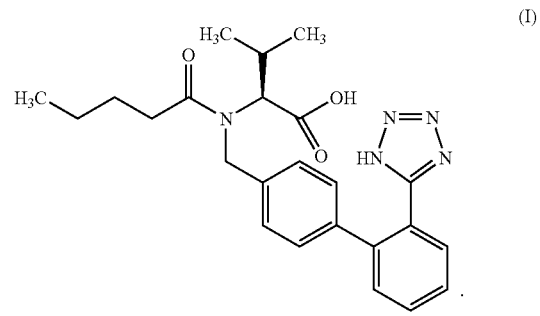

25 Claims, No Drawings

PROCESS FOR PREPARATION OF VALSARTAN

FIELD OF THE INVENTION

The present invention provides a novel cost effective and industrial process for the preparation of the antihypertensive agent valsartan.

BACKGROUND OF THE INVENTION

Valsartan, the generic name for N-(1-oxopentyl)-N-[[2'-(1H-tetrazol-5-yl)[1,1'-biphenyl]-4-yl]methyl]-L-valine (denoted as formula I below) is a well known nonpeptide angiotensin II $AT_1$-receptor antagonist and is on the market as Diovan or Tareg for the treatment of hypertension.

According to U.S. Pat. No. 5,399,578 and Bioorganic & Medicinal Chemistry Letters, vol. 4, No. 1, pp. 29-34, 1994, valsartan is prepared by the following reaction steps.

L-valine methyl ester hydrochoride is N-alkylated with 4-bromomethyl-2'-cyanobiphenyl, the product 4-[(2'-cyanobiphenyl-4-yl)methyl]-(L)-valine methyl ester thus formed is N-acylated with valeryl chloride to give N-[(2'-cyanobiphenyl-4-yl)methyl]-N-valeryl-(L)-valine methyl ester. N-[(2'-cyanobiphenyl-4-yl)methyl]-N-valeryl-(L)-valine methyl ester is treated with tributyltin azide to give valsartan methyl ester, which is then hydrolyzed under alkaline condition to give finally valsartan.

4-[(2'-Cyanobiphenyl-4-yl)methyl]-(L)-valine methyl ester may also be prepared by reductive amination of 2'-cyanobiphenyl-4-carbaldehyde with L-valine methyl ester using sodium cyanoborohydride.

The above process requires chromatographic techniques to isolate/purify the intermediates, particularly those that are formed in N-alkylation, N-acylation and tetrazole formation steps.

Since it requires chromatographic separations in many stages, the above process is complicated in operation and large-scale equipment is required, which results in poor productivity. In view of these drawbacks, the above process can hardly be said to be an advantageous one from the industrial production viewpoint.

According to U.S. Pat. No. 5,399,578 and Bioorganic & Medicinal Chemistry Letters, vol. 4, No. 1, pp. 29-34, 1994, valsartan is also prepared by the following reaction steps.

L-valine benzyl ester hydrochoride is N-alkylated with 4-bromomethyl-2'-cyanobiphenyl, the product 4-[(2'-cyanobiphenyl-4-yl)methyl]-(L)-valine benzyl ester so formed is N-acylated with valeryl chloride to give N-[(2'-cyanobiphenyl-4-yl)methyl]-N-valeryl-(L)-valine benzyl ester. N-[(2'-cyanobiphenyl-4-yl)methyl]-N-valeryl-(L)-valine benzyl ester is treated with tributyltin azide to give valsartan benzyl ester. Valsartan benzyl ester is subjected to catalytic hydrogenation using for example palladium-charcoal as catalyst to give valsartan.

Even though no chromatographic separations are required, the process just mentioned above, too, can hardly be said to be advantageous from the viewpoint of economy because of the use of costly hydrogenating catalysts like palladium-charcoal.

The processes described in the prior art are represented in the scheme shown below.

Thus, there is a need to develop a simple method for economically preparing valsartan and a pharmaceutically acceptable salt thereof having high quality with high yield in a commercial scale.

Debenzylation of a benzyl ester is usually effected by catalytic hydrogenation of the benzyl ester, preferred catalyst being palladium-charcoal.

Surprisingly, we have discovered that substituted or unsubstituted phenyl methyl ester of valsartan can be hydrolyzed with alkali metal hydroxides followed by acidification to give valsartan. This novel process does not use costly hydrogenating catalysts such as palladium-charcoal and is amicable for commercial production.

It is therefore an object of the present invention to provide a cost-effective process for the preparation of valsartan and pharmaceutically acceptable salts thereof, the said process being amicable for commercial production.

Scheme:

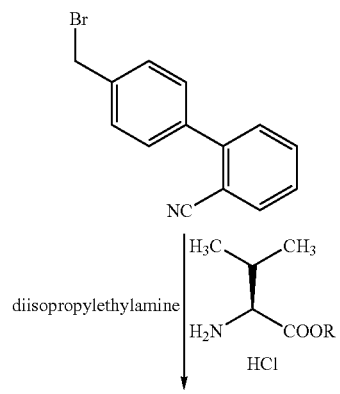

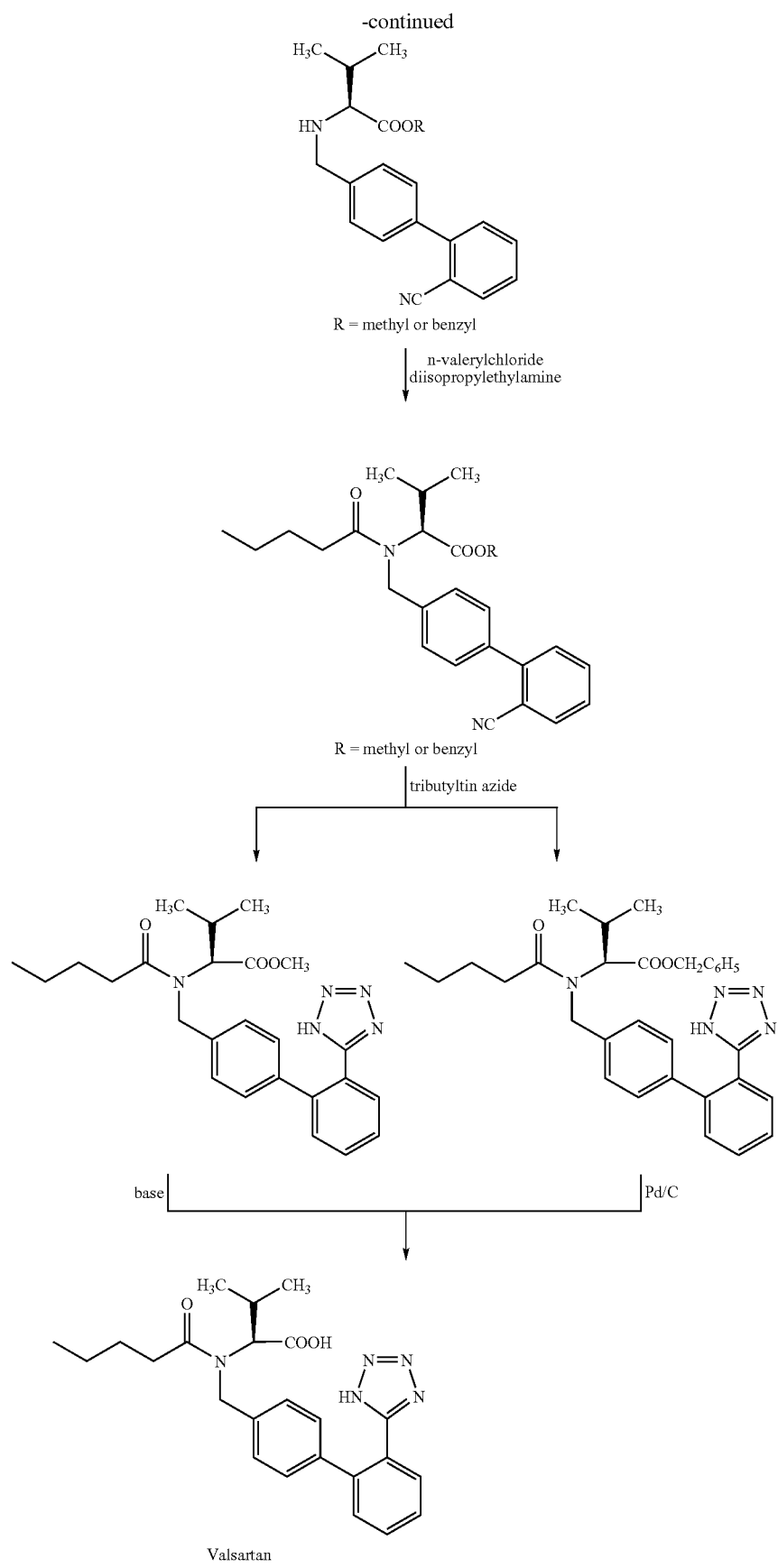

SUMMARY OF THE INVENTION

The present invention provides a process for preparing valsartan of formula I;

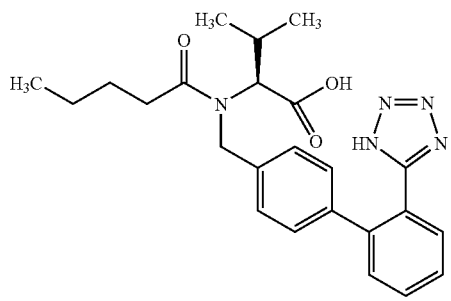

from a compound of the general formula II:

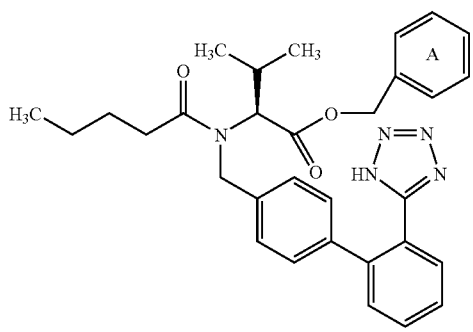

wherein ring A is substituted or unsubstituted phenyl group, which comprises:
a) hydrolyzing the compound of the general formula II with an excess alkali metal hydroxide;
b) washing the aqueous layer containing reaction products of step (a) with an organic solvent;
c) acidifying the aqueous layer using an acid; and
d) isolating valsartan of formula I from the reaction mixture of step (c).

In hydrolysis step, the compound of the general formula II, wherein the ring A is unsubstituted phenyl is preferred.

Preferably, the alkali metal hydroxide is sodium hydroxide or potassium hydroxide.

While the hydrolysis can be conducted in an aqueous system, it is also possible to conduct the hydrolysis in a mixed solution composed of water and a hydrophilic organic solvent. The hydrophilic organic solvents to be contained are not particularly restricted. There may be mentioned alcohols such as methanol, ethanol, propanol, isopropanol and tert-butanol.

Any organic solvent that can extract unreacted ester and/or phenyl or substituted phenyl methyl alcohol may be used in step (b). The organic solvent may be selected from hydrocarbons such as benzene, toluene, xylene, n-hexane, n-heptane, cyclohexane and petroleum ether; ethers such as diethyl ether, diisopropyl ether and tert-butyl methyl ether. Preferable organic solvents are n-heptane, cyclohexane, n-hexane, petroleum ether and diisopropyl ether.

In the step (c), the acid is added to the aqueous layer of the step (b) to bring the pH of the reaction mass below about 7.0, preferably to about 4.0 to 1.0 and more preferably to about 3.0 to 1.0.

Preferable acid is hydrochloric acid or sulfuric acid.

Valsartan is isolated in step (d) by extracting into an organic solvent followed by removing the solvent or precipitating valsartan.

Any organic solvent that can extract valsartan from the aqueous layer may be used. The organic solvent used in this step may be same as or different from that used in step (b) and is selected from chlorinated solvents such as methylene dichloride, chloroform, carbon tetrachloride and ethylene dichloride; esters such as ethyl acetate, methyl acetate, isopropyl acetate, tert-butyl acetate, ethyl formate, methyl formate. Preferable organic solvents are methylene dichloride, chloroform and ethyl acetate.

Valsartan is optionally converted to a pharmaceutically acceptable salt thereof. Some examples of the salts of valsartan are monosodium salt, monopotassium salt, dipotassium salt, magnesium salt, calcium salt and like.

The substituted phenyl group represents mono or poly substituted by, for example alkyl, halo, hydroxyl or nitro group. Preferable substituents are m-fluoro and m-nitro groups.

The excess alkali metal hydroxide refers to alkali metal hydroxide in an amount of more than 1 molar equivalents relative to the compound of the formula II, preferably about 2 to 20 molar equivalents relative to the compound of the formula II, more preferably about 3 to 8 molar equivalents relative to the compound of the formula II.

DETAILED DESCRIPTION OF THE INVENTION

The present invention provides a process for preparing valsartan of formula I:

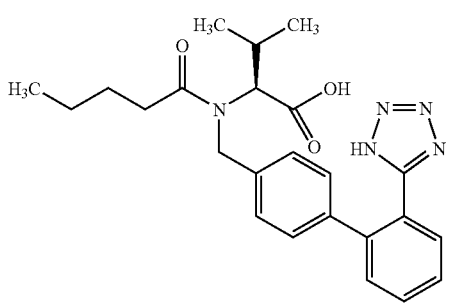

In the first step, a compound of the general formula II is hydrolyzed using more than one molar equivalent (excess) of alkali metal hydroxide.

In the general formula II:

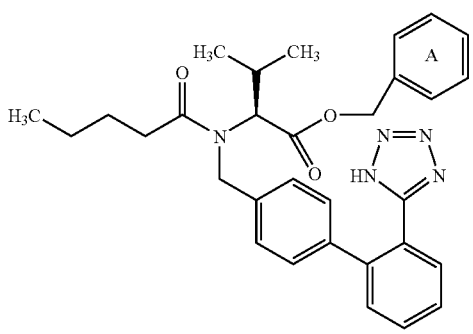

ring A is substituted or unsubstituted phenyl group. The substituted phenyl group represents mono or poly substituted by, for example alkyl, halo, hydroxyl or nitro group. Preferable substituents are m-fluoro and m-nitro groups. Preferably, ring A is phenyl group.

The compounds of the formula II can be prepared by the methods described, for example, in U.S. Pat. No. 5,399,578.

Alkali metal hydroxide to be used for hydrolyzing the compounds of the formula II is preferably sodium hydroxide or potassium hydroxide.

The alkali metal hydroxide is used in an amount of more than one molar equivalent is required for the hydrolysis of a compound of the formula II. The hydroxide is used in an amount of more than 1 molar equivalents relative to the compound of the formula II, preferably about 2 to 20 molar equivalents relative to the compound of the formula II, more preferably about 3 to 8 molar equivalents relative to the compound of the formula II.

While the hydrolysis can be conducted in an aqueous system, it is also possible to conduct the hydrolysis in a mixed solution composed of water and a hydrophilic organic solvent. The hydrophilic organic solvents to be contained are not particularly restricted. There may be mentioned alcohols such as methanol, ethanol, propanol, isopropanol and tert-butanol.

As regards the operation temperature in the hydrolysis step, the hydrolysis step is conducted preferably between 0° C. to reflux temperature, more preferably between 25° C. to reflux temperature and most preferably 50° C. to reflux temperature.

Usually the hydrolysis is conducted till the reaction is almost complete. Generally 1 to 10 hours is required for completion of the reaction. The progress of the reaction can be monitored by liquid chromatography.

In the second step, the reaction products of the hydrolysis contained in aqueous medium is washed with an organic solvent.

Any organic solvent that can extract unreacted ester and/or by-products like phenyl or substituted phenyl methyl alcohol may be used. The organic solvent may be selected from hydrocarbons such as benzene, toluene, xylene, n-hexane, n-heptane, cyclohexane and petroleum ether; ethers such as diethyl ether, diisopropyl ether and tert-butyl methyl ether. Preferable organic solvents are n-heptane, cyclohexane, n-hexane, petroleum ether and diisopropyl ether.

In the third step, the aqueous layer from the second step is acidified using an acid. Preferably, hydrochloric acid or sulfuric acid is used. The acid is added till the pH of the reaction mixture is decreased to below 7.0, preferably to about 4.0 to 1.0 and more preferably to about 3.0 to 1.0.

In the fourth step, valsartan formed in the third step is isolated from the reaction mixture.

The isolation is effected first by extracting valsartan of formula I from the aqueous layer into an organic solvent.

Any organic solvent that can extract valsartan from the aqueous layer may be used. The organic solvent used in this step may be same as or different from that used in second step and is selected from chlorinated solvents such as methylene dichloride, chloroform, carbon tetrachloride and ethylene dichloride; esters such as ethyl acetate, methyl acetate, isopropyl acetate, tert-butyl acetate, ethyl formate, methyl formate. A mixture of two or more organic solvents may also be used. Preferable organic solvents are methylene dichloride, chloroform and ethyl acetate.

Then, valsartan of formula I may be separated from the organic solvent by removal of the organic solvent by the techniques like distillation, vacuum drying, freeze drying and spray drying.

Valsartan of formula I may also be separated from the organic solvent by precipitating valsartan from the organic solvent by the techniques like partial removal of the organic solvent, lowering the temperature or using of an anti-solvent or combination thereof. The precipitation may optionally be initiated by seeding the organic solution.

Valsartan of formula I may preferably be separated from the organic solvent by employing both the techniques that is first removing the organic solvents, taking isolated valsartan into same or different organic solvent and then precipitating valsartan.

Valsartan is optionally converted to a pharmaceutically acceptable salt thereof by any conventional means. There may be mentioned the following valsartan salts: monosodium salt, monopotassium salt, dipotassium salt, magnesium salt, calcium salt and like.

The invention will now be further described by the following example, which is illustrative rather than limiting.

EXAMPLE

Valsartan benzyl ester (100 gm), water (800 ml) and sodium hydroxide (50 gm) are mixed and stirred for dissolution. The solution is heated to 65° C. and maintained for 2 hours 30 minutes at 60° C. to 65° C. The reaction mass is cooled to 25° C. and then washed with n-heptane (800 ml). The pH of the separated aqueous layer is adjusted to 2.0 by adding dilute hydrochloric acid at 20° C. to 25° C. Then the aqueous layer is extracted with methylene dichloride (1100 ml). Methylene dichloride layer is washed with water (1600 ml) and then with 10% sodium chloride solution (300 ml). Methylene dichloride layer is dried using sodium sulfate and then distilled under vacuum at 60° C. to give 90 gm of residue.

The residue is added to a mixture of ethyl acetate (235 ml) and diisopropyl ether (235 ml) and heated to reflux. Then the reaction mass is treated with activated charcoal, filtered through hyflobed and washed with diisopropyl ether (80 ml) and ethyl acetate (80 ml) at 50° C. The clear filtrate is cooled to 25° C. and stirred for 2 hours at 25° C. to 30° C. Then a further quantity of diisopropyl ether (720 ml) is added, maintained for 10 hours at 20° C. to 25° C., cooled to 0° C. and maintained for 2 hours at 0° C. to 5° C. Then filtered the contents, washed with chilled diisopropyl ether (100 ml) and dried to give 50 gm of 99.7% pure valsartan.

We claim:

1. A process for the preparation of valsartan of formula I:

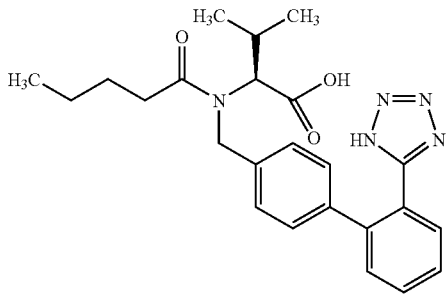

which comprises the steps of:
a) hydrolyzing the compound of the general formula II:

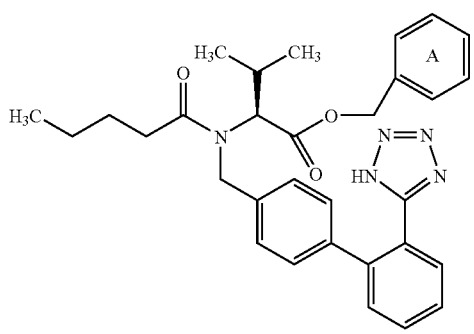

wherein ring A is substituted or unsubstituted phenyl group,
with an excess alkali metal hydroxide;
b) washing the aqueous layer containing reaction products of step (a) with an organic solvent;
c) acidifying the aqueous layer using an acid; and
d) isolating valsartan of formula I from the reaction mixture of step (c).

2. A process according to claim 1, wherein the ring A is phenyl.

3. A process according to claim 1, wherein the ring A is alkyl, halo, hydroxyl or nitro substituted phenyl.

4. A process according to claim 3, wherein the ring A is m-nitro phenyl or m-fluoro phenyl.

5. A process according to claim 1, wherein the alkali metal hydroxide is sodium hydroxide or potassium hydroxide.

6. A process according to claim 1, wherein the alkali metal hydroxide is sodium hydroxide.

7. A process according to claim 1, wherein the alkali metal hydroxide is used in an amount more than one molar equivalent relative to the compound of the formula II.

8. A process according to claim 7, wherein the alkali metal hydroxide is about 2 to 20 molar equivalent relative to the compound of the formula II.

9. A process according to claim 8, wherein the alkali metal hydroxide is about 3 to 8 molar equivalent relative to the compound of the formula II.

10. A process according to claim 1, wherein the hydrolysis is conducted in a mixed solution composed of water and a hydrophilic organic solvent.

11. A process according to claim 10, wherein the hydrophilic organic solvent is selected from methanol, ethanol, propanol, isopropanol and tert-butanol.

12. A process according to claim 1, wherein the organic solvent is selected from benzene, toluene, xylene, n-hexane, n-heptane, cyclohexane, petroleum ether, diethyl ether, diisopropyl ether, tert-butyl methyl ether and a mixture thereof.

13. A process according to claim 12, wherein the organic solvent is selected from n-heptane, cyclohexane, n-hexane, petroleum ether and diisopropyl ether.

14. A process according to claim 13, wherein the organic solvent is n-heptane.

15. A process according to claim 13, wherein the organic solvent is diisopropyl ether.

16. A process according to claim 1, wherein the aqueous layer is acidified in step (c) to below about pH 7.0.

17. A process according to claim 16, wherein the aqueous layer is acidified to about pH 4.0 to 1.0.

18. A process according to claim 17, wherein the aqueous layer is acidified to about pH 3.0 to 1.0.

19. A process according to claim 1, wherein the acid used in step (c) is hydrochloric acid or sulfuric acid.

20. A process according to claim 19, wherein the acid is hydrochloric acid.

21. A process according to claim 1, wherein the valsartan is isolated in step (d) by extracting into an organic solvent followed by removing the solvent or precipitating valsartan.

22. A process according to claim 21, wherein the organic solvent is selected from methylene dichloride, chloroform, carbon tetrachloride, ethylene dichloride, ethyl acetate, methyl acetate, isopropyl acetate, tert-butyl acetate, ethyl formate, methyl formate and a mixture thereof.

23. A process according to claim 22, wherein the organic solvent is selected from methylene dichloride, chloroform and ethyl acetate.

24. A process according to claim 23, wherein the organic solvent is methylene dichloride and ethyl acetate.

25. A process according to claim 23, wherein the organic solvent is ethyl acetate.

* * * * *